United States Patent
Metz et al.

(10) Patent No.: US 7,152,785 B2
(45) Date of Patent: Dec. 26, 2006

(54) PATIENT-CENTRIC DATA ACQUISITION PROTOCOL SELECTION AND IDENTIFICATION TAGS THEREFOR

(75) Inventors: Stephen Wayne Metz, Greenfield, WI (US); Christopher D. Unger, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 126 days.

(21) Appl. No.: 10/730,788

(22) Filed: Dec. 9, 2003

(65) Prior Publication Data

US 2005/0121505 A1    Jun. 9, 2005

(51) Int. Cl.
*G06K 5/00* (2006.01)

(52) U.S. Cl. .................. 235/380; 235/375; 235/486; 705/3

(58) Field of Classification Search .............. 235/375, 235/380, 486; 705/2, 3; 600/300
See application file for complete search history.

(56) References Cited

U.S. PATENT DOCUMENTS

| | | | | |
|---|---|---|---|---|
| 5,513,101 | A * | 4/1996 | Pinsky et al. ............... 705/3 |
| 5,586,262 | A * | 12/1996 | Komatsu et al. ............ 705/2 |
| 5,592,374 | A * | 1/1997 | Fellegara et al. ........... 705/3 |
| 5,781,442 | A | 7/1998 | Engleson et al. |
| 5,823,948 | A * | 10/1998 | Ross et al. ................ 600/300 |
| 5,865,745 | A * | 2/1999 | Schmitt et al. ............ 600/407 |
| 5,917,536 | A * | 6/1999 | Kunimoto et al. .......... 347/247 |
| 5,950,207 | A * | 9/1999 | Mortimore et al. ....... 707/104.1 |
| 6,021,393 | A * | 2/2000 | Honda et al. ................ 705/3 |
| 6,068,192 | A * | 5/2000 | McCabe et al. ............ 235/487 |
| 6,157,914 | A * | 12/2000 | Seto et al. ................... 705/3 |
| 6,161,757 | A * | 12/2000 | Morris ...................... 235/375 |
| 6,272,469 | B1 * | 8/2001 | Koritzinsky et al. .......... 705/2 |
| 6,431,440 | B1 * | 8/2002 | Tsuchino ................... 235/380 |
| 6,434,572 | B1 * | 8/2002 | Derzay et al. ........... 707/104.1 |
| 6,464,636 | B1 * | 10/2002 | Kinicki et al. ............. 600/437 |
| 6,497,358 | B1 * | 12/2002 | Walsh ....................... 235/380 |
| 6,506,155 | B1 * | 1/2003 | Sluis .......................... 600/437 |
| 6,519,569 | B1 * | 2/2003 | White et al. .................. 705/3 |
| 6,538,831 | B1 * | 3/2003 | Ikeda ......................... 360/32 |
| 6,656,118 | B1 * | 12/2003 | Sharma et al. ............. 600/437 |
| 6,656,120 | B1 * | 12/2003 | Lee et al. ................... 600/437 |
| 6,795,572 | B1 * | 9/2004 | Matsuno .................... 382/132 |
| 2003/0061071 | A1 * | 3/2003 | Babula et al. ............... 705/2 |
| 2003/0125988 | A1 * | 7/2003 | Rao et al. .................... 705/3 |
| 2003/0139944 | A1 * | 7/2003 | Carlsen et al. ............... 705/2 |
| 2004/0017894 | A1 * | 1/2004 | Takasawa .................. 378/116 |

\* cited by examiner

*Primary Examiner*—Ahshik Kim
(74) *Attorney, Agent, or Firm*—Clements Walker; Christopher L. Bernard; Peter J. Vogel

(57) ABSTRACT

Patient-centric data acquisition protocol selection systems and methods, and identification tags therefor, are described. Embodiments comprise a patient-centric data acquisition protocol selection system comprising: a programmable identification tag capable of allowing predetermined information about a patient to be stored therein and retrieved therefrom; a medical imaging system capable of communicating with the programmable identification tag; and programming associated with the medical imaging system for selecting an optimal data acquisition protocol; wherein the medical imaging system reads information from the programmable identification tag and then the programming selects an optimal data acquisition protocol based, at least in part, on the predetermined information about the patient that is stored in the programmable identification tag.

24 Claims, 2 Drawing Sheets

PATIENT-CENTRIC DATA ACQUISITION PROTOCOL SELECTION AND IDENTIFICATION TAGS THEREFOR

FIELD OF THE INVENTION

The present invention relates generally to medical imaging. More specifically, the present invention relates to patient-centric data acquisition protocol selection systems and methods that utilize an identification tag to allow a patient's information to be automatically transferred to a medical imaging device so that an optimal data acquisition protocol can be selected based, at least in part, upon the information stored in the patient's identification tag.

BACKGROUND OF THE INVENTION

With applications ranging from diagnostic procedures to radiation therapy, the importance of high-performance medical imaging is immeasurable. As such, new advanced medical imaging technologies continue to be developed.

Numerous modalities currently exist for medical imaging, including: ultrasound, magnetic resonance imaging, x-ray, computed tomography, positron emission tomography, etc. Such modalities may comprise either film-based or digital imaging systems, with digital imaging systems representing the future of medical imaging. Digital imaging systems produce far more accurate and detailed images of an object than conventional film-based imaging systems, and also allow further enhancements of the images to be made once an object is scanned. While the quantity and quality of imaging modalities has recently exploded, an increasing number of patients are now having repeat imaging examinations, either in the same modality or in different modalities. Additionally, it is now possible to use information from prior imaging examinations to determine patient information for use in prescribing new imaging examinations and selecting data acquisition protocols therefor.

Each imaging technique, whether film-based or digital, requires various data acquisition protocols to be selected and input to the medical imaging device prior to scanning the patient to acquire an image. Generally, these data acquisition protocols are selected by a scanner technician, who inputs various information about a patient into the system, evaluates the information, and then selects an appropriate protocol based thereon. Inputting this information into a system is prone to errors. Additionally, selecting an appropriate protocol is highly subjective, and therefore, it is difficult to train technicians on optimal protocol selection. As the quality of the resulting scan or image is often highly dependent upon the information that is input and the data acquisition protocol that is selected, it would be beneficial to have a way to automatically transfer patient information to a scanner, as well as select an optimal patient-centric data acquisition protocol for each patient, thereby removing the proneness to errors and subjectivity of the data acquisition protocol selection process.

SUMMARY OF THE INVENTION

Accordingly, the above-identified shortcomings of existing data acquisition protocol selection systems and methods are overcome by embodiments of the present invention, which relates to patient-centric data acquisition protocol selection systems and methods that utilize identification tags to allow patient information to be automatically transferred to a scanner, where an optimal patient-centric data acquisition protocol can be selected for each patient based, at least in part, on each patient's own information, which is often derived from the image or parametric data contained in the patient's prior medical imaging scans.

Embodiments of this invention comprise patient-centric data acquisition protocol selection systems comprising: a programmable identification tag capable of allowing predetermined information about a patient to be stored therein and retrieved therefrom; a medical imaging system capable of communicating with the programmable identification tag; and programming associated with the medical imaging system for selecting an optimal data acquisition protocol; wherein the medical imaging system reads information from the programmable identification tag and then the programming selects an optimal data acquisition protocol based, at least in part, on the predetermined information about the patient that is stored in the programmable identification tag.

The predetermined information may comprise: a patient's name, a patient's address, a patient's age, a patient's phone number, a patient's e-mail address, a patient's gender, a patient's social security number, a patient's height, a patient's weight, a patient's allergies, a patient's medical insurance information, a patient's emergency contact information, a patient's medical history, a patient's contraindications, a previous protocol used on the patient, a patient's previous reactions to oral or intravenous contrast agents or other medicines, a previous medical image of the patient, information derived from a previous medical image of the patient, a patient's fat percent, a patient's organ location, a patient's bone mineral density, a patient's body composition, a diagnosis from a patient's medical history, a treatment from a patient's medical history, an operator comment on a prior protocol used, and/or demographic information related to a patient.

The medical imaging system may comprise: an ultrasound system, a magnetic resonance imaging system, an x-ray system, a computed tomography system, a positron emission tomography system, a nuclear medicine system, and/or combinations thereof.

The programmable identification tag may further comprise a security feature capable of restricting access to the identification tag to predetermined systems or individuals. The patient-centric data acquisition protocol selection system may further comprise: updating means for saving new information to the programmable identification tag.

The predetermined information may be automatically transferred between the programmable identification tag and the medical imaging system upon the occurrence of a predetermined event, such as when the programmable identification tag enters a predetermined area, when the programmable identification tag gets within a predetermined distance of a device capable of reading from or writing to the programmable identification tag, when the programmable identification tag is connected to the medical imaging system, and/or upon command.

The programmable identification tag may comprise a pin, a bracelet, a necklace, a badge, a card, and/or a patch. The programmable identification tag may further comprise at least one monitor.

Embodiments of this invention also comprise patient-centric data acquisition protocol selection methods, comprising the steps of: providing an identification tag to a patient, the identification tag being capable of storing predetermined information about the patient therein and allowing the stored predetermined information about the patient to be retrieved therefrom; transferring the predetermined information about the patient from the identification tag to a medical imaging system; selecting an optimal data acquisition protocol based, at least in part, on the predetermined information about the patient that is transferred to the medical imaging system; performing a medical imaging scan of the patient utilizing the optimal data acquisition protocol; and generating an image of an area of interest of the patient from data acquired during the medical imaging scan.

The patient-centric data acquisition protocol selection method may further comprise storing results of the medical imaging scan of the patient on the identification tag.

These patient-centric data acquisition protocol selection methods may comprise selecting an optimal data acquisition protocol by utilizing programming to automatically select the optimal data acquisition protocol for a given situation.

The optimal data acquisition protocol may be selected based on the predetermined information about the patient that is stored in the identification tag and at least one of: a doctor's desired diagnostic result, and previous data acquisition protocols utilized in similar situations.

Embodiments of this invention also comprise medical imaging systems, which comprise: an identification tag associated therewith, comprising: means for storing predetermined information therein; means for allowing the predetermined information to be transferred to the medical imaging system upon the occurrence of a predetermined event; and means for allowing new information to be stored in the patient-centric identification tag; and programming associated with the medical imaging system for selecting an optimal data acquisition protocol based, at least in part, on the predetermined information that is transferred from the patient-centric identification tag to the medical imaging system.

The means for storing predetermined information therein may comprise read/write memory and/or data storage blocks. The means for allowing the predetermined information to be transferred to the medical imaging system may comprise a radio frequency transmitter/receiver, an infra-red transmitter/receiver, and/or a land-based communications cable.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DESCRIPTION OF THE DRAWINGS

The systems and methods of the present invention are described herein below with reference to various figures, in which.

DETAILED DESCRIPTION OF THE INVENTION

Figure 1:
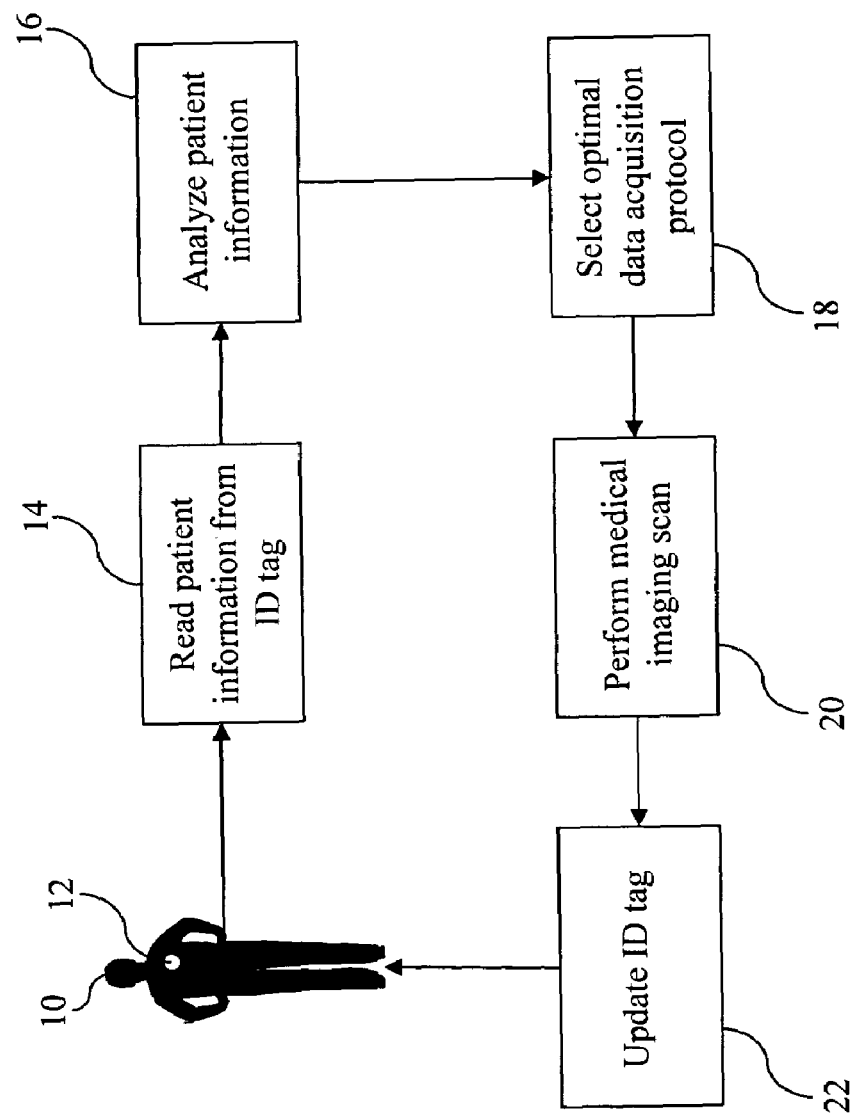
FIG. 1 is a flowchart showing the information flow utilized in embodiments of this invention.
Figure 2:
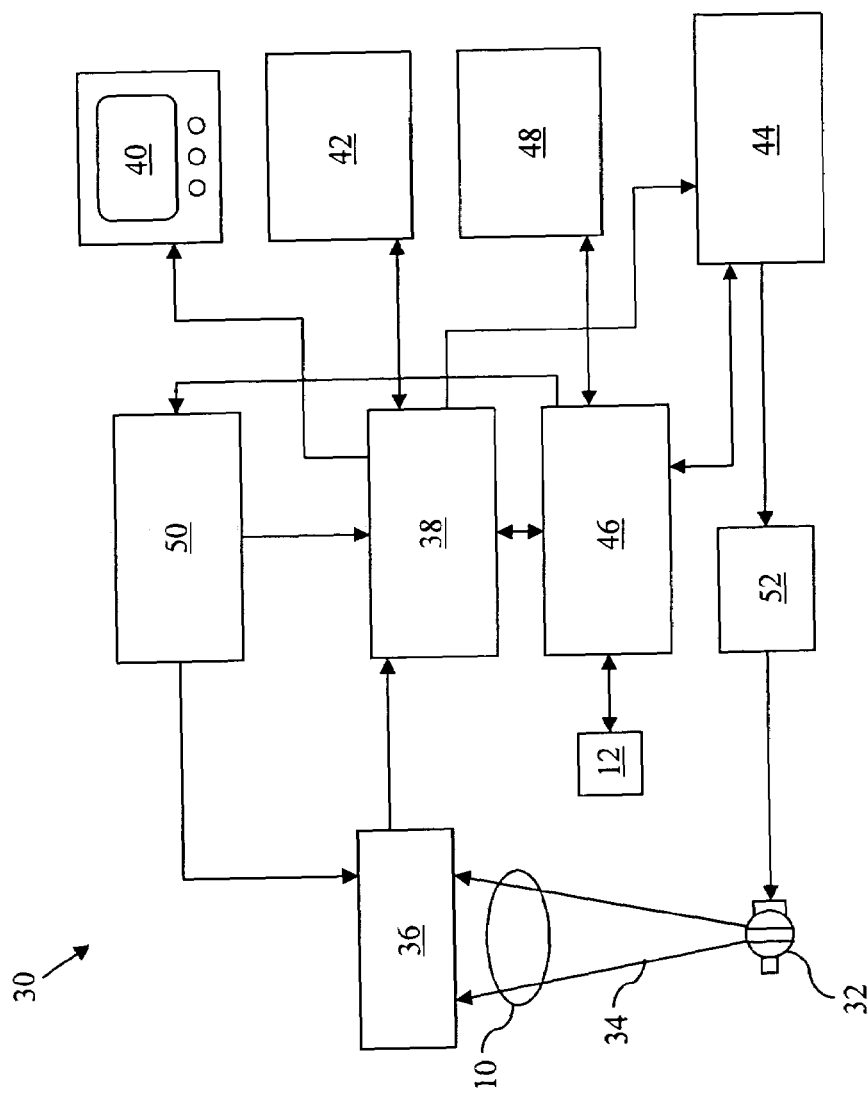
FIG. 2 is a schematic diagram showing the architecture of an exemplary medical imaging system, as utilized in embodiments of this invention.

For the purposes of promoting an understanding of the invention, reference will now be made to some preferred embodiments of the present invention as illustrated in FIGS. 1–2 and specific language used to describe the same. The terminology used herein is for the purpose of description, not limitation. Specific structural and functional details disclosed herein are not to be interpreted as limiting, but merely as a basis for the claims as a representative basis for teaching one skilled in the art to variously employ the present invention. Any modifications or variations in the depicted structures and methods, and such further applications of the principles of the invention as illustrated herein, as would normally occur to one skilled in the art, are considered to be within the spirit and scope of this invention.

This invention relates to patient-centric data acquisition protocol selection systems and methods that utilize an identification tag to allow a patient's information to be automatically transferred to a medical imaging device so that an optimal data acquisition protocol can be selected based, at least in part, upon the information stored in the patient's identification tag. These identification tags may be used in a variety of medical imaging modalities, such as, but not limited to, ultrasound, magnetic resonance imaging, x-ray, computed tomography, positron emission tomography, nuclear medicine, and/or combinations thereof. Those skilled in the relevant arts will appreciate the manner in which these various modalities can be used to acquire the desired medical image. Therefore, a detailed explanation of these systems, and the manners in which they operate, is not provided herein in the interest of brevity. These identification tags reduce the possibility of errors that can be caused by inputting improper information, and also take the subjective guesswork out of selecting an optimal data acquisition protocol for a given medical imaging device.

When a patient enters a medical facility or medical transport vehicle, they may be given an identification tag, which may be in any suitable form, such as, but not limited to, a pin, a bracelet, a necklace, a badge, a card, or a patch, etc. This identification tag may comprise "smart chip" microprocessor technology and have read/write memory and/or data storage blocks so that predetermined information can be saved thereto and retrieved therefrom when desired. The smart chip may contain various information of interest about the patient, such as, but not limited to, the patient's electronic health record, which may comprise the patient's name, age, address, phone numbers, e-mail addresses, sex, social security number, height, weight, allergies, medical insurance information, emergency contact information, the patient's medical history, contraindications, previous protocols used on the patient, previous reactions to oral or intravenous contrast agents or other medicines, and previous medical images of the patient and/or information derived thereby (i.e., fat percent, organ location, bone mineral density, body composition, etc.). This smart chip may also contain information such as the diagnoses and treatments from the patient's medical history, operator comments on the prior protocols used (i.e., what worked, what could have been improved, etc.), demographic information related to the patient, and/or any other suitable information that may aid in the optimal selection of data acquisition protocols.

The information that is stored in a patient's identification tag may come from various locations, such as for example, from the patient's health record in the hospital information system (HIS), radiology information system (RIS), or clinical information system (CIS), among other places. The information may also be obtained from the patient directly or from a friend or family member, for example, at a patient data entry station at the medical facility, or it may be obtained in an ambulance while the patient is being transported to the medical facility. In some embodiments, an identification tag may be created for a patient automatically as they pass by or over a biometric scanner that reads certain information from the patient and then automatically creates an identification tag based thereon. In some embodiments, instead of having an identification tag, biometrics such as facial recognition, finger or palm print recognition, and/or iris or retina recognition may be used to identify a patient, locate a patient number, and retrieve information about the patient that may be stored elsewhere, such as in a central database. In some embodiments, the identification tag may comprise only the patient identification, and the rest of the information may be stored elsewhere, such as for example, in a central HIS, RIS or CIS database or the like.

The information may be stored in the identification tag in any suitable format, such as for example, in a keyword format such as XML, so that information can be easily shared and transferred from system to system and from scanner to scanner.

The identification tags may comprise any suitable type of communications device capable of allowing information to be transmitted from and received by the identification tags, such as, but not limited to, a land-based communications cable (i.e., coaxial cable, fiber-optic cable, etc.), or a wireless radio frequency or infrared transmitter and receiver. Additionally, bar codes or other optical encodings means, such as holographs, may be utilized in embodiments of this invention to facilitate the transmission of information thereto and therefrom.

In embodiments, the identification tag may comprise monitors therein for monitoring various physiologic parameters of interest, such as body temperature, pulse rate, blood pressure, etc. These parameters can be used for patient monitoring directly, or they may be used to set acquisition parameters. For example, the pulse rate monitor can be used to set acquisition parameters. The stability of the pulse rate can also be used to determine the type of gating or reconstruction algorithm that will be used.

In embodiments, the identification tag may be read by a system automatically as a patient enters a predetermined area (i.e., when the patient enters the medical facility, when the patient enters the scanner exam room, or when a patient gets within a certain distance of a device capable of reading from and/or writing to the identification tag, etc.). After a scan is complete, the results thereof may be transferred from the medical imaging system to the identification tag, where it can be stored therein. In other embodiments, the identification tag may be read from or written to when prompted by a medical imaging system or other suitable computer system.

In embodiments, the identification tags may also comprise security features to ensure that the information stored therein can only be accessed and/or modified by authorized systems or individuals.

Referring now to FIG. 1, there is shown a flowchart showing the information flow utilized in embodiments of this invention. First, a patient 10 enters a medical facility or medical transport vehicle with an identification tag 12. If a patient 10 does not have an identification tag 12, one can be created for them. Thereafter, when the patient 10 arrives for their medical imaging scan, the information contained in the patient's identification tag 12 can be read and/or downloaded 14 to a computer system such as a computer system associated with the medical imaging device. The patient's information can then be analyzed 16 by the computer system, and an optimal data acquisition protocol can then be selected 18 based, at least in part, on the patient's information that is stored in their identification tag 12. Thereafter, the patient 10 can be scanned 20, and then their identification tag 12 can be updated 22 to include the new scan information and any other relevant information. In this manner, the patient's identification tag 12 is kept up-to-date for any additional scans that may be needed, or for the patient's next visit to the medical facility. This process may be repeated as needed.

When selecting the optimal protocol for a given situation 18, the computer system may query relevant databases associated therewith for information about previous protocols that worked with other patients in similar situations. The computer system may also query for prior protocols for the patient 10, or indicate any issues or concerns that were associated with prior protocols. Then, the computer system may use this information, together with the doctor's desired diagnostic result and the patient's information, to select the optimal data acquisition protocol for the present situation 18.

Once a system is set up with the appropriate programming and/or software, updates thereto may be available via the Internet or in any other suitable manner. For example, embodiments of this invention may allow access to the latest available protocol selection technology via the Internet (i.e., via websites and/or via automatic subscription updates).

Referring now to FIG. 2, there is shown a schematic diagram showing the architecture of an exemplary medical imaging system 30, as utilized in embodiments of this invention. In this exemplary non-limiting embodiment, the medical imaging system 30 is an x-ray system. These x-ray systems 30 generally comprise an x-ray source 32, an x-ray detector 36, and an x-ray detector controller 50 that contains electronics for operating the x-ray detector 36. During operation, x-rays 34 are directed from the x-ray source 32 towards the x-ray detector 36. After passing through an object being imaged (i.e., a patient 10), the x-rays 34 fall upon the detector 36, where the x-rays 34 are converted to an electrical charge. This electrical charge is then sent to an image processor 38, where the image signal is processed and enhanced. The processed image may then be displayed on a cathode ray tube display 40, or other suitable display, and/or the image can be stored in mass storage 42 for later retrieval. The image processor 38 can also produce a brightness control signal which can be applied to an exposure control circuit 44 to regulate the power supply 52, which can thereby regulate the x-ray source 32. The overall operation of the x-ray system 30 may be governed by a system controller 46, which may receive commands from operator interface 48. Operator interface 48 may comprise a keyboard, touchpad, or other suitable input device. An associated cathode ray tube display 40 (or other suitable display) may allow the operator to view the reconstructed image and other data from the image processor 38. The operator supplied commands and parameters may be used by the system controller 46 to provide control signals and information to the image processor 38, the x-ray detector controller 50, the exposure control circuit 44, and/or the identification tag 12.

Embodiments of the present invention may make use of software or firmware running on the system controller 46 to carry out the processing of data in the methods and systems of this invention. A mouse, pointing device, or other suitable input device may be employed to facilitate the entry of data and/or image locations. Other embodiments of this invention may utilize a general purpose computer or workstation having a memory and/or printing capability for storing or printing images. Suitable memory devices are well known and include, but are not limited to, RAM, diskettes, hard drives, optical media, etc. Embodiments using stand-alone computers or workstations may receive data therefrom via conventional electronic storage media and/or via a conventional communications link, and images may then be reconstructed therefrom.

The identification tags 12 of this invention may communicate in any suitable manner with the system controller 46. For example, a patient's identification tag 12 may be read automatically via an IR or RF link when the patient 10 enters a specific area (i.e., the medical facility lobby, the medical imaging scanner room, etc.). Alternatively, the information stored on a patient's identification tag 12 may be read when prompted by the system controller 46. There will be less chance of errors by transferring the information directly from the identification tag to the system controller 46, as opposed to having a technician manually enter the information into the system controller 46. Once a patient's information is downloaded to the system controller 46, the information may be analyzed, other relevant information may be considered, and then an optimal data acquisition protocol may be selected. Allowing the system controller 46 or other suitable computer to select the optimal data acquisition protocol removes the subjectivity of the selection process.

As described above, this invention allows optimal data acquisition protocols to be selected more quickly and more accurately than currently possible, which can consequently improve the performance of the medical imaging devices they are utilized in. Additionally, this invention reduces the need to train scanner technicians about proper data acquisition protocol selection. Advantageously, this invention utilizes an identification tag to automatically transfer information about a patient to a medical imaging system, thereby reducing the chance of errors caused from manually inputting the information. Many other advantages will also be apparent to those skilled in the relevant art.

Various embodiments of this invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. For example, while the embodiments shown and described herein were utilized in x-ray imaging, this invention may be utilized for other types of medical imaging without deviating from the spirit and scope of this invention, and all such variations are intended to be covered herein. Thus, it is intended that the present invention cover all suitable modifications and variations as come within the scope of the appended claims and their equivalents.

What is claimed is:

1. A patient-centric data acquisition protocol selection system, comprising:
    a programmable identification tag storing predetermined information about a patient wherein the predetermined information is selectively retrieved therefrom, said predetermined information including at least one prior acquisition protocol;
    a medical imaging system in communication with the programmable identification tag;
    programming associated with the medical imaging system for automatically selecting an optimal data acquisition protocol; and
    a database storing reference information about other patients and data acquisition protocols associated therewith;
    wherein the medical imaging system selectively reads the predetermined information from the programmable identification tag and then the programming automatically selects the optimal data acquisition protocol based on the predetermined information about the patient, including said at least one prior acquisition protocol that is stored in the programmable identification tag and the reference information about the other patients and the data acquisition protocols associated therewith that is stored in the database.

2. The patient-centric data acquisition protocol selection system of claim 1, wherein the predetermined information comprises at least one of: a patient's name, a patient's address, a patient's age, a patient's phone number, a patient's e-mail address, a patient's gender, a patient's social security number, a patient's height, a patient's weight, a patient's allergies, a patient's medical insurance information, a patient's emergency contact information, a patient's medical history, a patient's contraindications, a previous protocol used on the patient, a patient's previous reactions to oral or intravenous contrast agents or other medicines, a previous medical image of the patient, information derived from a previous medical image of the patient, a patient's fat percent, a patient's organ location, a patient's bone mineral density, a patient's body composition, a diagnosis from a patient's medical history, a treatment from a patient's medical history, an operator comment on a prior protocol used, and demographic information related to a patient.

3. The patient-centric data acquisition protocol selection system of claim 1, wherein the medical imaging system comprises at least one of: an ultrasound system, a magnetic resonance imaging system, an x-ray system, a computed tomography system, a positron emission tomography system, a nuclear medicine system, and combinations thereof.

4. The patient-centric data acquisition protocol selection system of claim 1, wherein the programmable identification tag further comprises a security feature capable of restricting access to the identification tag to predetermined systems or individuals.

5. The patient-centric data acquisition protocol selection system of claim 1, further comprising:
    updating means for saving new information to the programmable identification tag.

6. The patient-centric data acquisition protocol selection system of claim 1, wherein the predetermined information is automatically transferred between the programmable identification tag and the medical imaging system upon the occurrence of a predetermined event.

7. The patient-centric data acquisition protocol selection system of claim 6, wherein the predetermined event comprises at least one of: the programmable identification tag enters a predetermined area, the programmable identification tag gets within a predetermined distance of a device capable of reading from or writing to the programmable identification tag, the programmable identification tag is connected to the medical imaging system, and upon command.

8. The patient-centric data acquisition protocol selection system of claim 1, wherein the programmable identification tag comprises at least one of: a pin, a bracelet, a necklace, a badge, a card, and a patch.

9. The patient-centric data acquisition protocol selection system of claim 1, wherein the programmable identification tag further comprises at least one monitor.

10. A patient-centric data acquisition protocol selection method, comprising the steps of:
    providing an identification tag to a patient, the identification tag storing predetermined information about the patient therein and allowing the stored predetermined information about the patient to be retrieved therefrom, said predetermined information including at least one prior acquisition protocol;

selectively transferring the predetermined information about the patient from the identification tag to a medical imaging system;

automatically selecting an optimal data acquisition protocol based on the predetermined information about the patient, including said at least one prior acquisition protocol that is transferred to the medical imaging system from the identification tag and reference information about other patients and data acquisition protocols associated therewith transferred to the medical imaging system from a database;

performing a medical imaging scan of the patient utilizing the optimal data acquisition protocol; and generating an image of an area of interest of the patient from data acquired during the medical imaging scan.

11. The patient-centric data acquisition protocol selection method of claim 10, wherein the predetermined information comprises at least one of: a patient's name, a patient's address, a patient's age, a patient's phone number, a patient's e-mail address, a patient's gender, a patient's social security number, a patient's height, a patient's weight, a patient's allergies, a patient's medical insurance information, a patient's emergency contact information, a patient's medical history, a patient's contraindications, a previous protocol used on the patient, a patient's previous reactions to oral or intravenous contrast agents or other medicines, a previous medical image of the patient, information derived from a previous medical image of the patient, a patient's fat percent, a patient's organ location, a patient's bone mineral density, a patient's body composition, a diagnosis from a patient's medical history, a treatment from a patient's medical history, an operator comment on a prior protocol used, and demographic information related to a patient.

12. The patient-centric data acquisition protocol selection method of claim 11, wherein the medical imaging system comprises at least one of: an ultrasound system, a magnetic resonance imaging system, an x-ray system, a computed tomography system, a positron emission tomography system, a nuclear medicine system, and combinations thereof.

13. The patient-centric data acquisition protocol selection method of claim 10, further comprising:

storing results of the medical imaging scan of the patient on the identification tag.

14. The patient-centric data acquisition protocol selection method of claim 10, wherein the predetermined information about the patient is transferred between the identification tag and the medical imaging system upon the occurrence of a predetermined event.

15. The patient-centric data acquisition protocol selection method of claim 14, wherein the predetermined event comprises at least one of: the identification tag enters a predetermined area, the identification tag gets within a predetermined distance of a device capable of reading from or writing to the identification tag, the identification tag is connected to the medical imaging system, the identification tag is prompted to transfer predetermined information therefrom, and upon command.

16. The patient-centric data acquisition protocol selection method of claim 10, wherein selecting an optimal data acquisition protocol comprises utilizing programming to automatically select the optimal data acquisition protocol for a given situation.

17. The patient-centric data acquisition protocol selection method of claim 16, wherein the optimal data acquisition protocol is selected based on the predetermined information about the patient that is stored in the identification tag and at least one of: a doctor's desired diagnostic result, and previous data acquisition protocols utilized in similar situations.

18. A medical imaging system, comprising:
an identification tag associated therewith, comprising:
means for storing predetermined information therein, said predetermined information including at least one prior acquisition protocol;
means for selectively transferring the predetermined information, including said at least one prior acquisition protocol to the medical imaging system upon the occurrence of a predetermined event;
means for selectively transferring reference information from a database to the medical imaging system; and
means for storing new information in the patient-centric identification tag; and
programming associated with the medical imaging system for automatically selecting an optimal data acquisition protocol based on the predetermined information, including said at least one prior acquisition protocol that is transferred from the patient-centric identification tag to the medical imaging system and the reference information that is transferred from the database to the medical imaging system.

19. The medical imaging system of claim 18, wherein the means for storing predetermined information therein comprises at least one of: read/write memory and data storage blocks.

20. The medical imaging system of claim 18, wherein the means for selectively transferring the predetermined information to the medical imaging system comprises at least one of the following: a radio frequency transmitter/receiver, an infra-red transmitter/receiver, and a land-based communications cable.

21. The medical imaging system of claim 18, wherein the predetermined information comprises at least one of: a patient's name, a patient's address, a patient's age, a patient's phone number, a patient's e-mail address, a patient's gender, a patient's social security number, a patient's height, a patient's weight, a patient's allergies, a patient's medical insurance information, a patient's emergency contact information, a patient's medical history, a patient's contraindications, a previous protocol used on the patient, a patient's previous reactions to oral or intravenous contrast agents or other medicines, a previous medical image of the patient, information derived from a previous medical image of the patient, a patient's fat percent, a patient's organ location, a patient's bone mineral density, a patient's body composition, a diagnosis from a patient's medical history, a treatment from a patient's medical history, an operator comment on a prior protocol used, and demographic information related to a patient.

22. The medical imaging system of claim 18, wherein the medical imaging system comprises at least one of: an ultrasound system, a magnetic resonance imaging system, an x-ray system, a computed tomography system, a positron emission tomography system, a nuclear medicine system, and combinations thereof.

23. The medical imaging system of claim 18, wherein the identification tag further comprises a security feature capable of restricting access to the identification tag to predetermined systems or individuals.

24. The medical imaging system of claim 18, wherein the predetermined event comprises at least one of: the identification tag enters a predetermined area, the identification tag gets within a predetermined distance of a device capable of reading from or writing to the identification tag, the identification tag is connected to the medical imaging system, the identification tag is prompted to transfer predetermined information therefrom, and upon command.

* * * * *